United States Patent
Carol et al.

(10) Patent No.: US 6,325,758 B1
(45) Date of Patent: *Dec. 4, 2001

(54) METHOD AND APPARATUS FOR TARGET POSITION VERIFICATION

(75) Inventors: Mark P. Carol, Sewickley; Robert C. Campbell, Cranberry Township; Brian S. Rosen, Mars; Richard E. Huber, Harmony; Richard V. Nash, Allison Park, all of PA (US)

(73) Assignee: Nomos Corporation, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,496

(22) Filed: Oct. 27, 1998

Related U.S. Application Data

(60) Provisional application No. 60/063,276, filed on Oct. 27, 1997.

(51) Int. Cl.[7] ....................................................... A61B 8/00
(52) U.S. Cl. ............................................. 600/439; 128/916
(58) Field of Search ..................................... 600/439, 407, 600/2–3, 7; 378/206, 65, 68–69; 364/413.21, 413.26; 601/2–4

(56) References Cited

U.S. PATENT DOCUMENTS

| | | | |
|---|---|---|---|
| 5,391,139 | * 2/1995 | Edmundson | 600/7 |
| 5,394,875 | * 3/1995 | Lewis et al. | 128/916 X |
| 5,411,026 | * 5/1995 | Carol | 600/439 |
| 5,447,154 | * 9/1995 | Cinquin et al. | 600/437 X |
| 5,690,107 | * 11/1997 | Hofmann | 378/206 |
| 5,810,007 | * 9/1998 | Holupka et al. | 600/439 |

* cited by examiner

Primary Examiner—Francis J. Jaworski
(74) Attorney, Agent, or Firm—Bracewell & Patterson, L.L.P.

(57) ABSTRACT

A method and apparatus for verifying the position of a target to be treated by a radiation therapy device may include an ultrasound probe used to generate ultrasound images of the target; a position sensing system for indicating the position of the ultrasound probe with respect to the radiation therapy device, whereby the location of the target with respect to the radiation therapy device is known; and the ultrasound image of the target may be aligned with radiation treatment data.

39 Claims, 6 Drawing Sheets

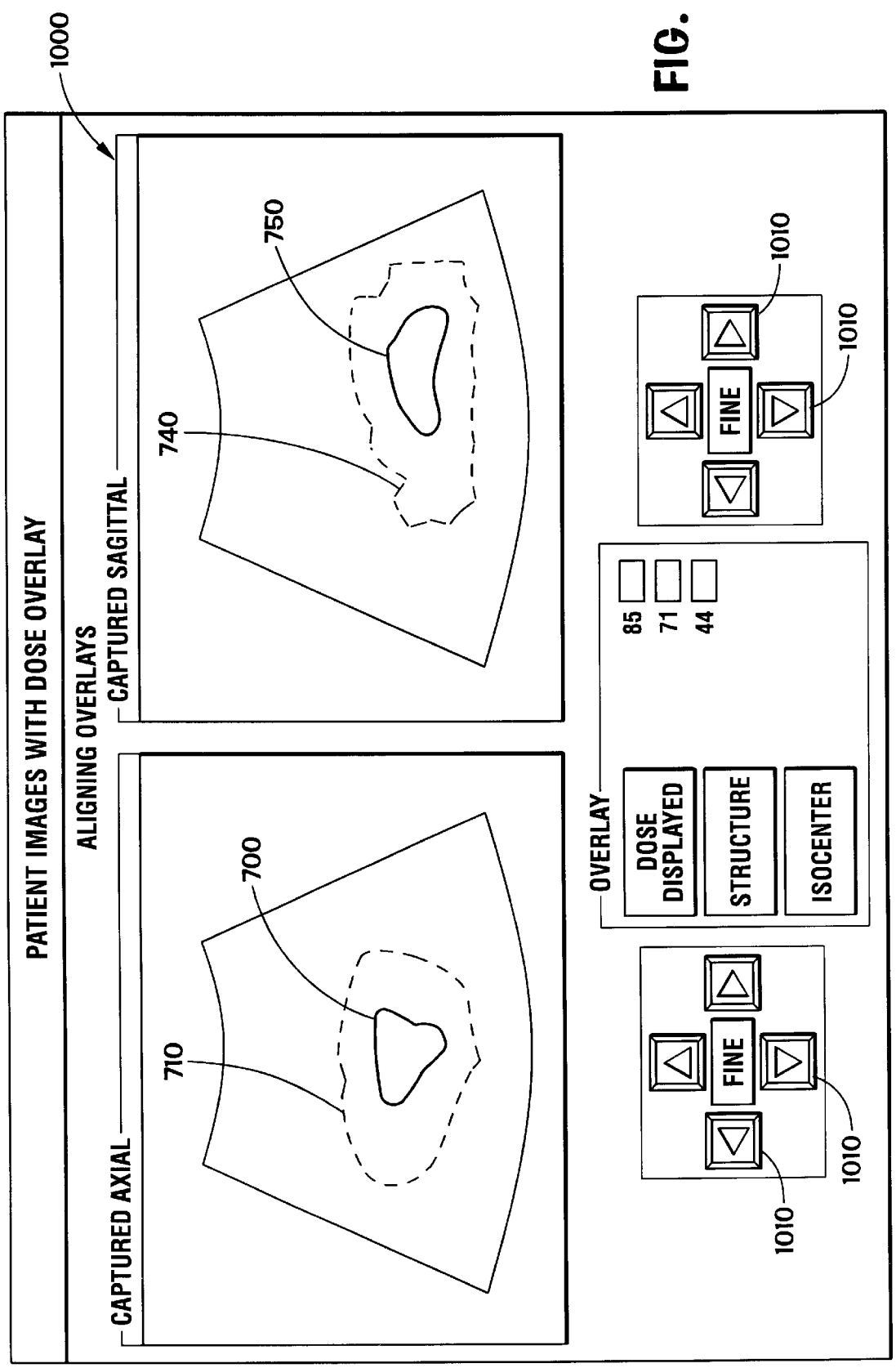

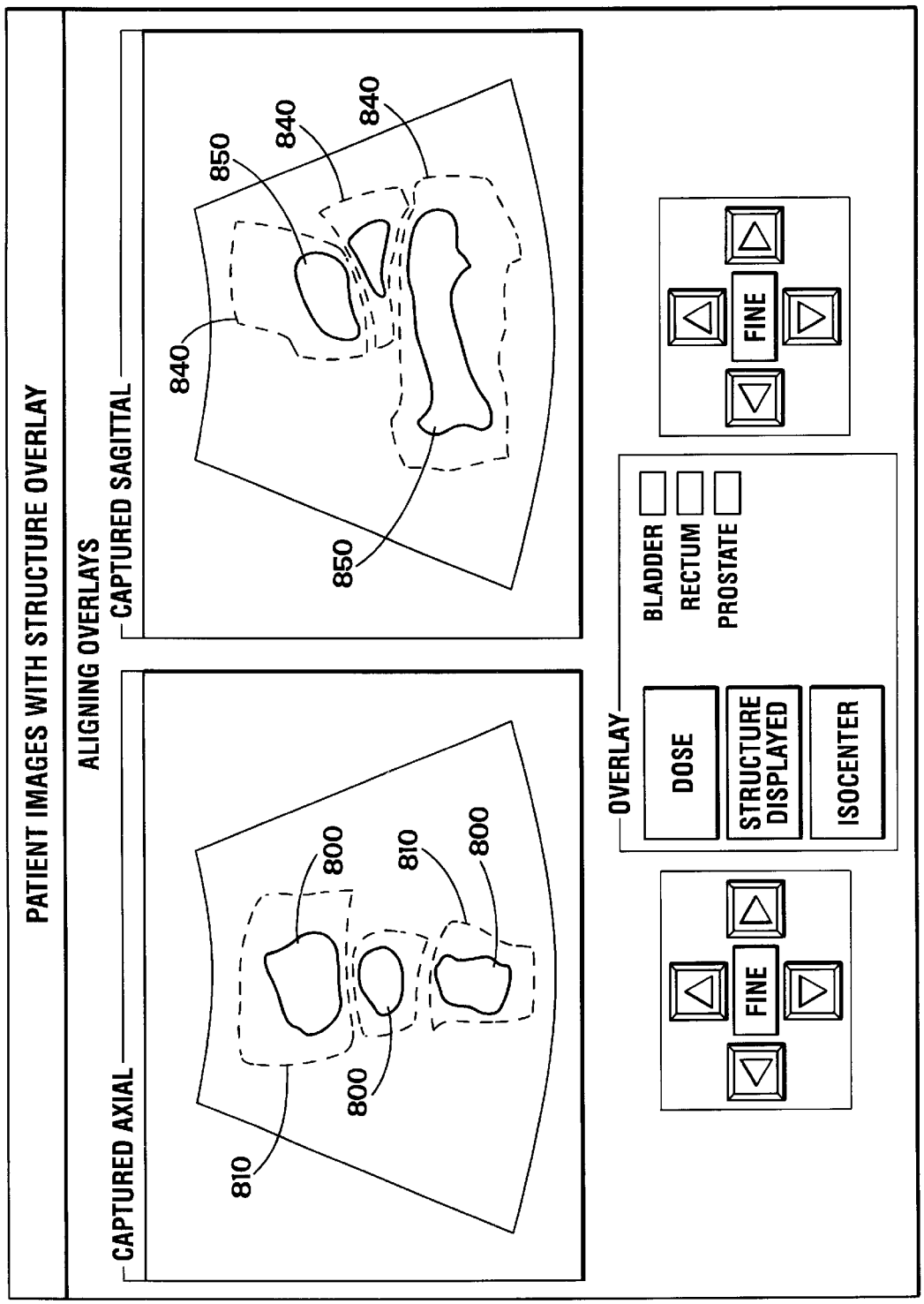

METHOD AND APPARATUS FOR TARGET POSITION VERIFICATION

RELATED APPLICATION

1. This application claims the benefit of U.S. provisional application Ser. No. 60/063,276, filed Oct. 27, 1997

BACKGROUND OF THE INVENTION

1. Field of the Invention

The invention relates to a method and apparatus for verifying the position of a target to be treated by a radiation therapy device operating in accordance with a radiation therapy plan.

2. Description of Related Art

Modern day radiation therapy of cancerous tumors has two goals: eradication of the tumor and avoidance of damage to healthy tissue and organs present near the tumor. It is believed that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of radiation therapy is to confine the delivered radiation dose to only the tumor volume defined by the outer surface of the tumor, while minimizing the dose of radiation to surrounding healthy tissue or adjacent healthy organs or structures.

Radiation therapy treatment typically uses a radiation delivery device such as a linear accelerator, or other radiation producing source, to treat the tumor. The radiation delivery device typically has a radiation beam source which is positioned about the patient and directs the radiation beam toward the tumor to be treated. Various types of devices have been proposed to conform the shape of the radiation treatment beam to follow the spatial contour of the tumor as seen by the radiation treatment beam, from a linear accelerator, as it passes through the patient's body into the tumor, during rotation of the radiation beam source, which is mounted on a rotatable gantry of the linear accelerator. Multileaf collimators, which have multiple leaf, or finger, projections which can be moved individually into and out of the path of the radiation beam, can be so programmed, and are examples of such devices. Various types of radiation treatment planning systems can create a radiation treatment plan, which when implemented will deliver a specified dose of radiation shaped to conform to the target, or tumor, volume, while limiting the radiation dose delivered to sensitive surrounding healthy tissue or adjacent healthy organs or structures.

A basic problem in radiation therapy is knowing where the target, or tumor, is located at the time the radiation therapy treatment is occurring. The use of the term "target" is intended to include not only a tumor or a body organ, or portion thereof, to be treated, but also an organ, sensitive body structure, or portion thereof to be avoided in the radiation therapy treatment. It is assumed that the patient's position and the target's position within the patient will be grossly, or nominally, the same at the time of radiation treatment, as it was at the time the radiation treatment plan was created. If the position of the target is not the same as it was at the time the treatment plan was determined, the dose of radiation may not be delivered to the correct location within the patient's body. Since patients are not always positioned properly on the treatment table of the radiation therapy device, which may be a linear accelerator or a cobalt unit, and since organs of a patient may move within the patient from day to day, the target may not be positioned at the exact location where the radiation therapy plan has assumed it would be located. Thus, present day radiation therapy plans typically regard the target to be treated to occupy a space in the patient's body which is larger than it really occupies, in order to insure that the target to be treated regardless of its location within the patient's body, falls within the volume of tissue which receives the desired radiation treatment dose. A disadvantage of such conventional radiation therapy plans is that there is a major concern associated with increasing the volume of tissue which is treated, to insure that the actual target to be treated receives the desired dose of radiation. Because some healthy tissue surrounds the target to be treated, or healthy organs, or sensitive structures, lie adjacent to the target to be treated, delivering the maximum desired radiation dose to this larger volume of tissue may occur and increase risk of damaging healthy tissue, healthy organs, or sensitive structures. This increased risk may cause oncologists to deliver a smaller radiation dose to the larger treatment volume, which is safer for the healthy tissue, with the potential disadvantage of underdosing the target to be treated.

Therefore, the art has sought a method and apparatus for verifying the position of a target, within a body of a patient for use in a radiation treatment plan, which: verifies that the position of the target in the radiation treatment plan is positioned to conform to the position of the target used in the radiation treatment plan; and prevents healthy tissue surrounding the target, or healthy organs and sensitive structures from being exposed to an undesired amount of radiation.

SUMMARY OF THE INVENTION

In accordance with the invention, the foregoing advantages have been achieved through the present method for verifying the position of a target, having an outer surface, within a body of a patient for use in a radiation treatment plan which includes at least two two-dimensional representations of treatment plan data corresponding to the target. The present invention includes the steps of: disposing the patient on a treatment table of a radiation therapy device; providing a means for generating an ultrasound image; generating at least two two-dimensional ultrasound images of the target in the patient's body, with the ultrasound image generating means being disposed in a known geometric orientation for each ultrasound image generated; displaying the ultrasound images of the target; displaying the representations of treatment plan data; aligning the displayed representations of treatment plan data with the displayed ultrasound images; and determining an amount and type of movement of the treatment table and/or radiation therapy device and/or patient required to dispose the target, with respect to the radiation therapy device, to conform to the desired position of the target in the radiation treatment plan.

Another feature of the present invention is that the displayed representations of treatment plan data may be a dose distribution contour, a structure contour, or geometric information concerning radiation beam projections or isocenter locations. A further feature of the present invention may include the step of moving the treatment table with respect to the radiation therapy device to dispose the target to conform to the desired position of the target in the radiation treatment plan. An additional feature of the present invention may include the step of repositioning the patient with respect to the treatment table to achieve rotational or translational alignment of the patient. An additional feature of the present invention may include the step of storing the treatment plan data, representations of treatment plan data, and ultrasound images for future use, including patient set-up, operator verification, physician review, and patient records.

Another feature of the present invention is that at least one of the ultrasound images may be a sagittal image, and the sagittal image may be utilized to guide the repositioning of the patient to achieve rotational alignment of the patient. A further feature of the present invention may include the step of utilizing, as the means for generating the ultrasound image, an ultrasound probe mounted to a 3-D digitizer articulated arm. Another feature of the present invention may include the step of disposing the 3-D digitizer articulated arm upon a moveable support. An additional feature of the present invention may include the step of disposing the ultrasound image generating means in the known geometric orientation by aligning the 3-D digitizer articulated arm to the radiation therapy device.

Another feature of the present invention is that the radiation therapy device may have a collimator, and the 3-D digitizer articulated arm is aligned to the radiation therapy device by releasably securing the 3-D digitizer articulated arm to the collimator. An additional feature of the present invention is the radiation therapy device may have a gantry, and the 3-D digitizer articulated arm may be aligned by identifying at least three points on the gantry by touching the 3-D digitizer articulated arm to the at least three points when the gantry is at a known position. Yet another feature of this present invention may include the steps of disposing the 3-D digitizer articulated arm upon a moveable support, providing holes in the floor adjacent the treatment table, and aligning the 3-D digitizer articulated arm by registering the moveable support and the 3-D digitizer articulated arm to the holes. Another feature of the present invention is that the at least two two-dimensional ultrasound images may include an axial image and a sagittal image.

In accordance with another aspect of the invention, the foregoing advantages have been achieved through the present target position verification system for use by a user with a radiation therapy device for treating a target within a body of a patient, and with a radiation treatment plan which includes at least two two-dimensional representations of treatment plan data with the location of the target and the representations of the treatment plan data being known. The target position verification system may include: an ultrasound probe for generating at least two two-dimensional ultrasound images of the target; a position sensing system for indicating the position of the ultrasound probe with respect to the radiation therapy device, whereby the location of the target with respect to the radiation therapy device is known; and a computer having a monitor associated therewith, adapted to: display on the monitor the ultrasound images of the target; display on the monitor the representations of treatment plan data; in response to user input, align the representations of treatment plan data with the ultrasound image; and in response to the alignment, determine the difference between the location of the target in the ultrasound images and the location of the target in representations of treatment plan data.

The target position verification system and method for verifying the position of a target of the present invention, have the advantages of preventing healthy tissue surrounding the tumor, or healthy organs or sensitive structures located adjacent the tumor, from being exposed to an undesired amount of radiation; and permit the verification that the position of the target with respect to the radiation therapy treatment device conforms to the desired position of the target in the radiation treatment plan.

BRIEF DESCRIPTION OF THE DRAWING

Figure 2:
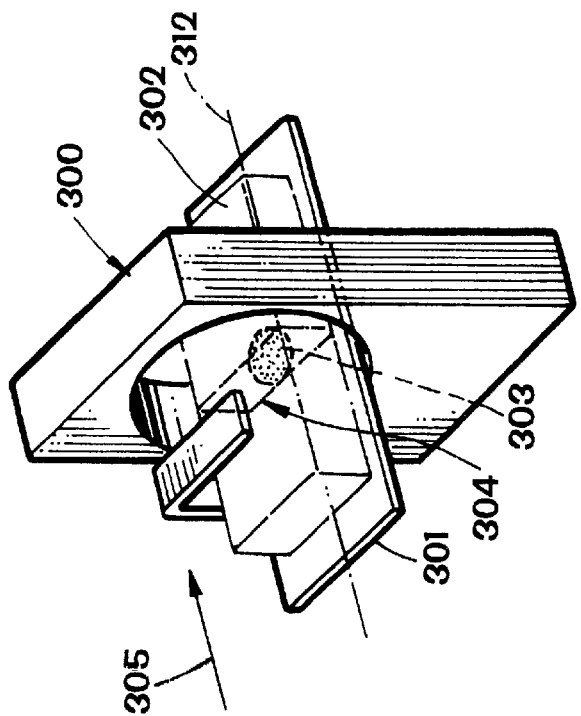
Figure 1:
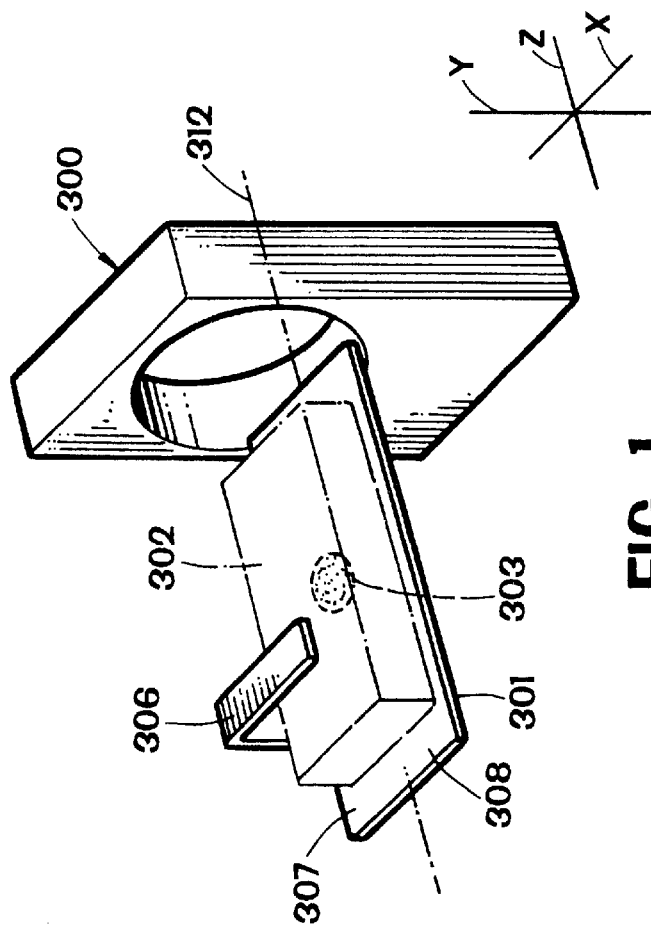
Figure 4:
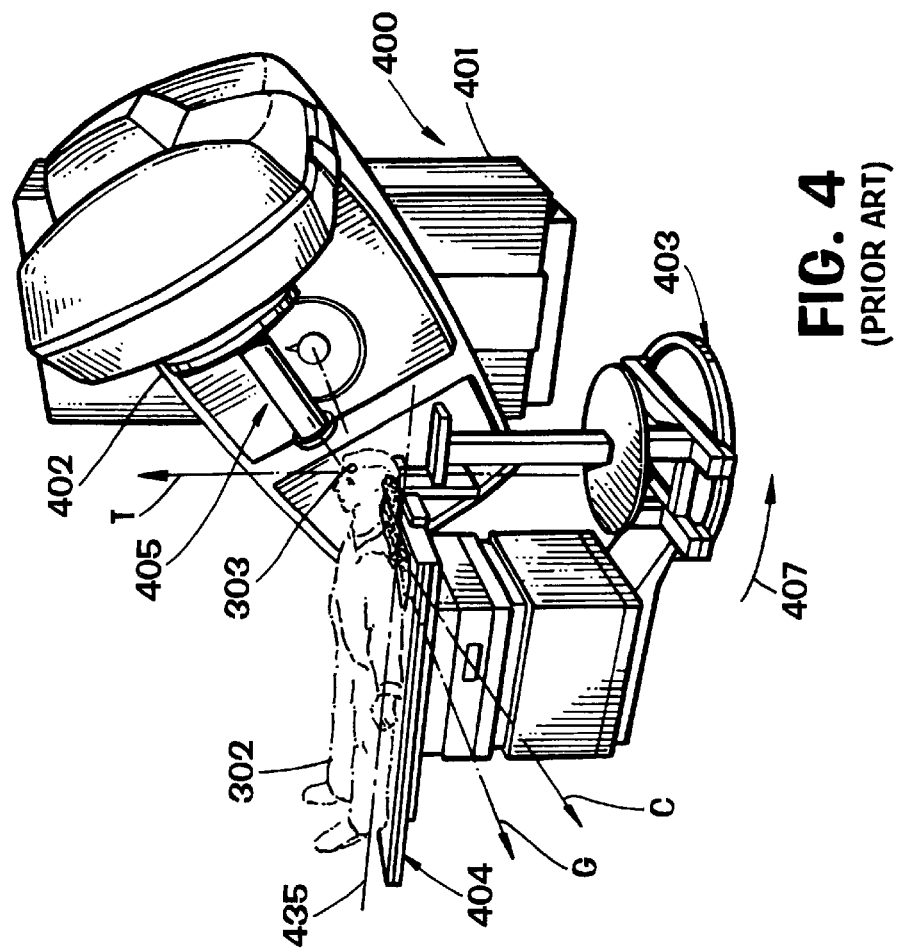
Figure 3:
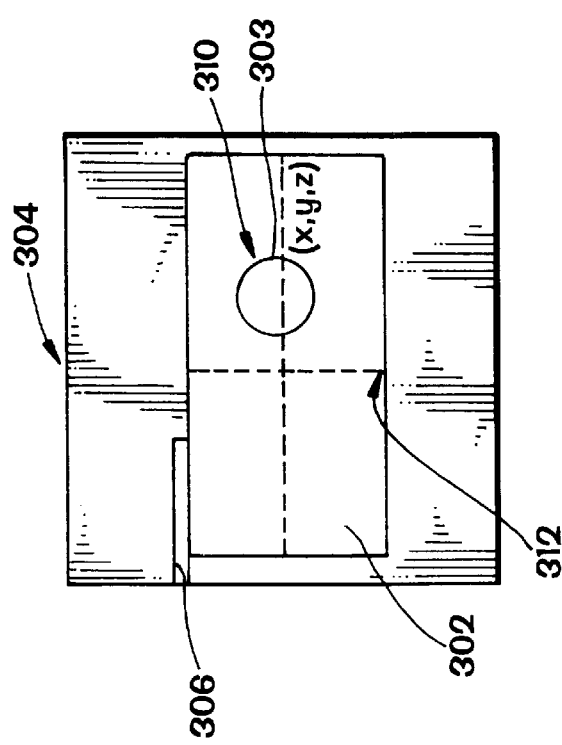
Figure 5:
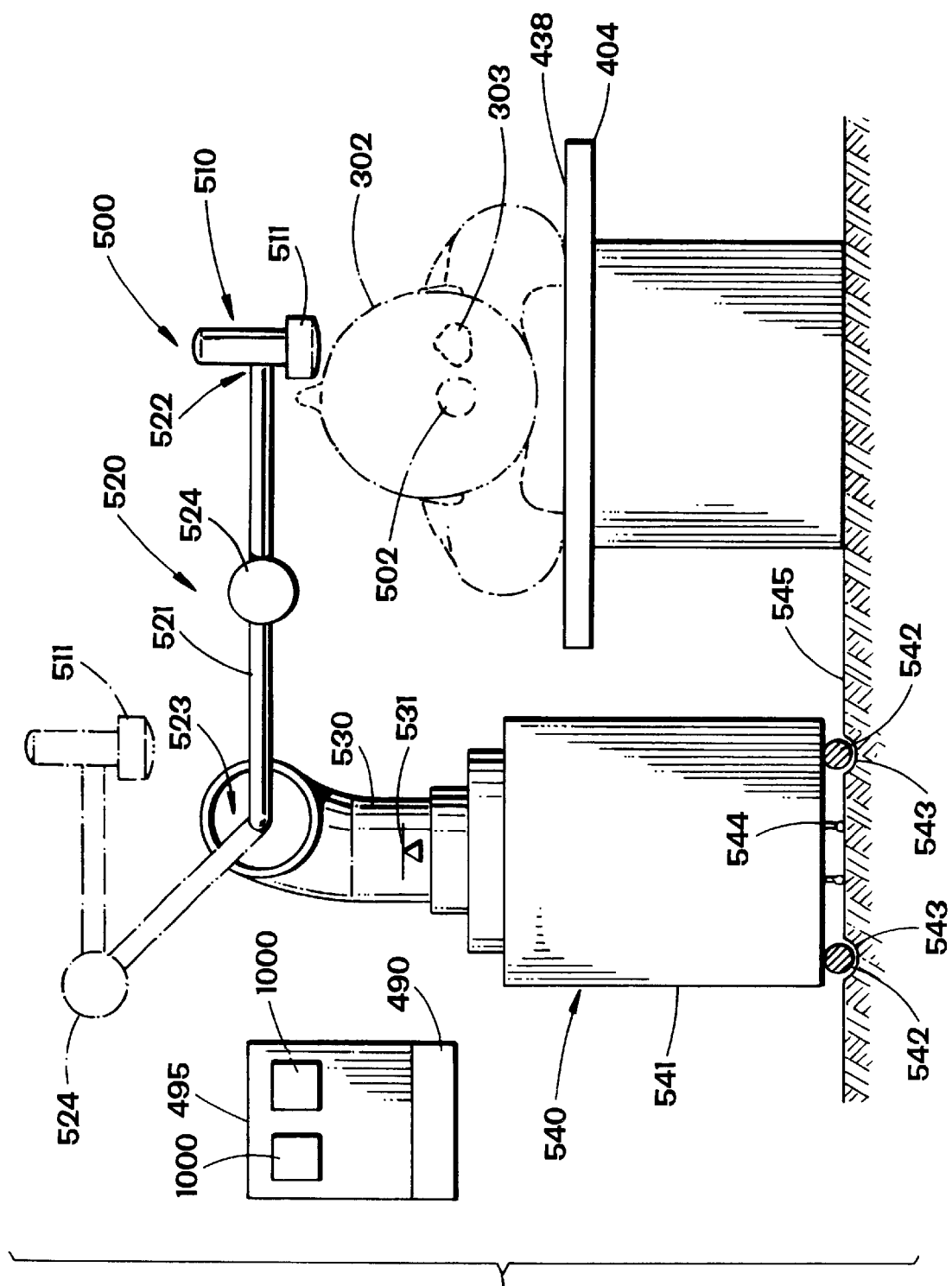
Figure 6:
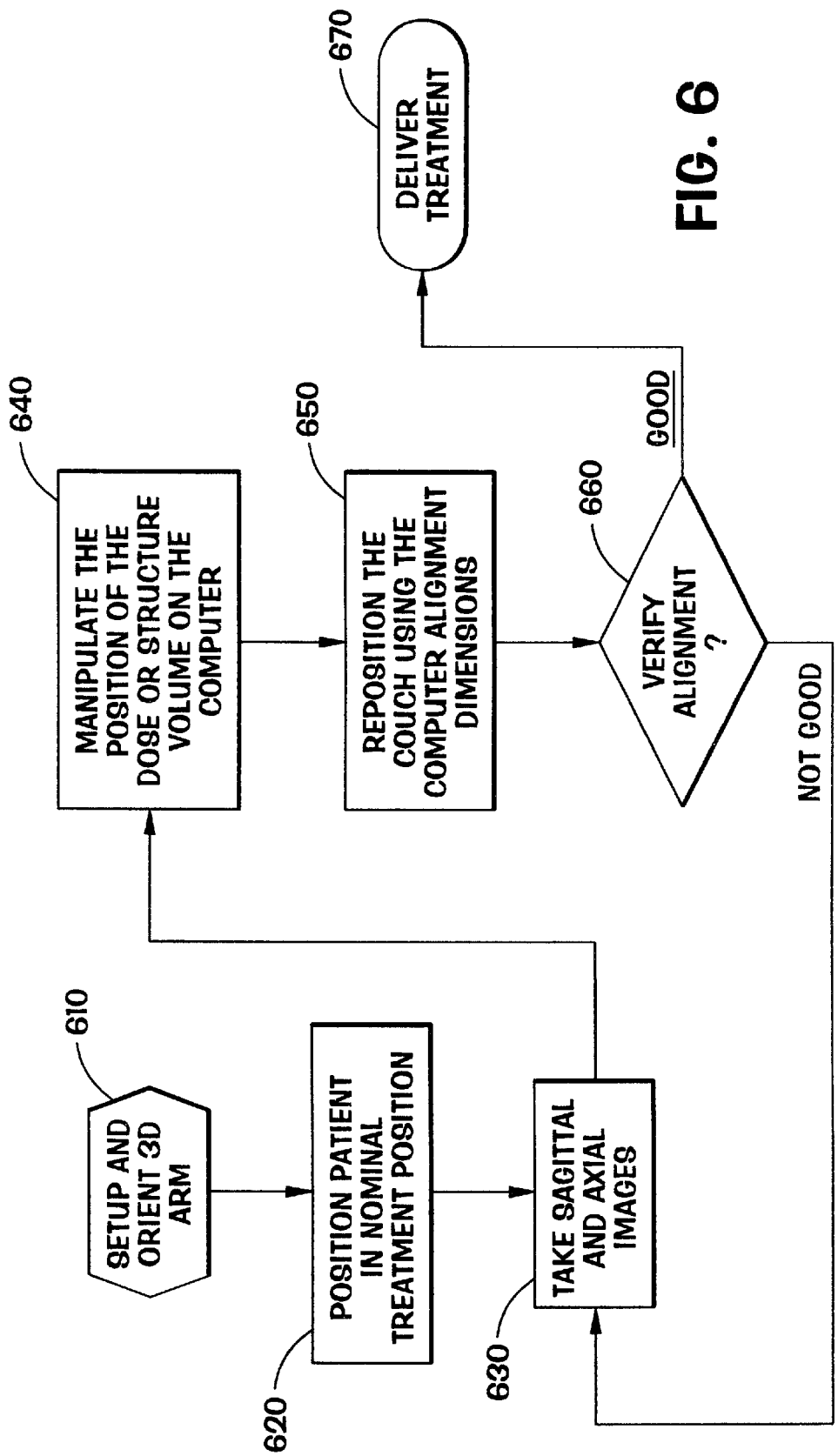

IN THE DRAWING:

FIG. 1 is a perspective view of a conventional imaging device with a patient schematically illustrated on the imaging table, the patient having a target disposed within the patient's body;

FIG. 2 is a perspective view of the imaging device of FIG. 1, with the patient passing through the imaging device;

FIG. 3 is an example of an image produced by the imaging device of FIG. 1, illustrating the position of the target within the patient's body;

FIG. 4 is a perspective view of a conventional radiation therapy device, or linear accelerator, including a rotatable couch, or treatment table, collimator, and gantry;

FIG. 5 is a side view of a target position verification system in accordance with the present invention, viewed along the longitudinal axis of treatment table of the radiation therapy device;

FIG. 6 is a flowchart illustrating the step-by-step method of the present invention;

FIG. 7 is a front view of a computer screen displaying two two-dimensional representations of treatment plan data being aligned with two two-dimensional ultrasound images of the target, wherein the representations of treatment plan data are dose distribution contours;

FIG. 8 is a view of a computer screen displaying two two-dimensional representations of treatment plan data being aligned with two two-dimensional ultrasound images of the target, wherein the representations of treatment plan data are structure contours.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

With reference to FIG. 1, a conventional imaging device 300 is schematically shown and includes a conventional imaging table 301, upon which is disposed a patient 302 having a tumor, or target, 303 within the patient's body 302. As previously discussed, the use of the term "target" throughout this specification, including the claims, includes, as appropriate, a tumor or an organ, or portion thereof, to be treated, or an organ, sensitive structure, or portion thereof, which is not to be treated in the radiation therapy plan. Imaging device 300 may be a computerized tomographic ("CT") scanning device, as illustrated in FIG. 1, or may alternatively be a magnetic resonance ("MR") imaging device, as are known in the art. CT scanning devices, such as imaging device 300, produce an image representing a "slice" of body tissue 304 (shown in phantom lines in FIG. 2), one such slice being illustrated in FIG. 3. A plurality of images, or diagnostic images, 304 are obtained by the imaging device 300, and this series of "slices", which constitute a complete CT study, represent a three-dimensional picture of a particular volume, or section, of the patient's body, such as that portion of the patient's body 302 which includes target 303 therein. The plurality of "slices", or diagnostic images, 304 are obtained by moving the patient 302, disposed upon imaging table 301, through imaging device 300 in the direction shown by arrow 305 as illustrated in FIG. 2.

If desired, as hereinafter described in greater detail, the orientation of the patient 302 upon imaging table 301 when the slices, or images, 304 are made, may be predetermined, or known, as by fixating the patient's body 302 to the imaging table 301 by use of a conventional fixation device 306. Fixation device 306, illustrated schematically in FIGS. 1 and 2, and as shown in the slice, or image 304, of FIG. 3, may be any conventional invasive, or noninvasive, fixation device which attaches to the patient 302 a coordinate system and secures the patient to the imaging table 301. Typically, the coordinate system is one which is forced by its attachment mechanism to be coplanar with the plane 307 in which lies the upper surface 308 of imaging table 301; however, any fixation device 306 having a coordinate system may be utilized provided the relationship between the coordinate system and the imaging table 301 is known, when it is desired to fixate patient 302.

In FIG. 3, the target 303 is shown disposed within the patient's body 302 at a particular location having conventional X, Y, and Z coordinates, which are determined in a conventional manner by the CT scanner with respect to the frame of reference, or the coordinate system, of the imaging device as shown by its X, Y and Z axes in FIG. 1. The cross-sectional configuration of target 303 in FIG. 3 appears as circular, for illustrative purposes only.

After the series of slices, or images, 304 of the patient's body 302 which include target 303 therein, are obtained, the series of slices, or diagnostic images are then transferred in a conventional manner to a conventional radiation treatment planning system which includes conventional software to permit a physician to two-dimensionally outline the outer surface 310 of target 303 in each slice 304. The computer software of the radiation treatment planning system may also construct, or create, a three-dimensional rendering of the outer surface 310 of target 303 from the plurality of slices, or diagnostic images, 304. In the case of imaging device 300 of FIG. 1, its frame of reference is the longitudinal axis 312, or Z axis, of imaging table 301. In a conventional manner, a radiation treatment plan is generated by the radiation treatment planning system, whereby target 303 may receive the necessary radiation dose to properly treat target 303. The radiation treatment plan could be, if desired, a conformal radiation treatment plan, whereby the shape of the radiation beam will conform to the spacial contour, or outline, 310 of target 303 as seen by the radiation beam as it passes through the target 303, or the "beam's eye view" of the target 303 during rotation of the radiation beam source about the target 303.

With reference to FIG. 4, a conventional radiation treatment device 400, which is preferably a conventional linear accelerator 401, includes a gantry 402, turntable 403 which causes treatment table 404 to rotate therewith, and a collimator 405, which preferably is a collimator capable of conforming the shape of the radiation beam to conform to the beam's eye view of the target being treated. The three axes of rotation of the gantry 402, turntable and treatment table 403, 404 and collimator 405 are designated with the letters G, T, and C, respectively. For illustrative purposes only, the target 303 within patient's body 302 is disposed in the patient's head in FIG. 4; however, the method and apparatus of the present invention may be used with targets disposed anywhere in the patient's body, that can be seen by the imaging device 300. The target 303 which is treated by linear accelerator 401 is disposed at the isocenter 406 of the linear accelerator 401. The isocenter 406 is defined as the point of intersection of the three axes of rotation, C, G, and T of linear accelerator 401. The previously described radiation treatment plan controls the operation of linear accelerator 401, and controls the operation of collimator 405, rotation of gantry 402, and location of treatment table 404, in a conventional manner. As previously discussed, the position and orientation of target 303 within patient's body 302 with respect to linear accelerator 401 may not necessarily be the same as the position and orientation of target 303 which was utilized in developing the radiation treatment plan. Thus, the present invention is used to verify that the position and orientation of target 303 within the patient's body 302 conforms, or matches, the position and orientation of the target 303 in the diagnostic slices 304 utilized in developing the radiation treatment plan.

With reference to FIG. 5, patient 302 is disposed on treatment table 404, with patient 302 laying flat upon treatment table 404, although patient 302 may not be laying precisely in the same orientation with respect to treatment table 404, as patient 302 had when patient 302 was lying upon imaging table 301. Patient 302 is laying on the upper surface 438 of treatment table 404, with the patient's spinal cord 502 being disposed substantially parallel with the longitudinal axis 435 of treatment table 404. Although it might be desirable to immobilize patient 302 during the radiation therapy treatment, due to the prolonged time required for many treatments, the patient's orientation on the treatment table 404 need not be precisely the same as its orientation on imaging table 301; however patient 302 is preferably laying flat on treatment table 404. Since the orientation of the patient's body 302 is not the same as it was when the patient 302 was imaged by imaging device 300, it should be apparent that it is very likely the position and orientation of target 303 with respect to treatment table 404 and linear accelerator 401 will not conform, or match, the position and orientation of target 303 upon which the radiation treatment plan for linear accelerator 401 has been based. It is thus necessary to verify the position of target 303 to determine if it will conform to its desired position which has been used in the radiation treatment plan previously obtained. Further, it is necessary to determine where to relocate target 303 with respect to linear accelerator 401, so that the position and orientation of target 303 will conform to its position and orientation required by the radiation treatment plan.

Still with reference to FIG. 5, the target verification system 500 of the present invention generally includes: a means for generating 510 at least two two-dimensional ultrasound images 700, 750, 800, 850 (FIGS. 7 and 8) of the target 303; a position sensing system 520 for indicating the position of the generating means 510 with respect to the radiation therapy device 400 (FIG. 4), whereby the location of the target 303 with respect to the radiation therapy device is known; and a computer 490 having a monitor 495 associated therewith. For illustrative purposes only, target 303 in FIG. 5 is located in the patient's prostate. Preferably, the means for generating 510 the ultrasound image, such as 700, is an ultrasound image generator, such as an ultrasound probe 511 and may be a commercially available ultrasound probe 511, Model 4.5/50 from Diasonics Vingmed Ultrasound, Inc. of Santa Clara, Calif. Ultrasound probe 511 can generate two-dimensional ultrasound images of the portion of the patient's body 302 containing target 303, while patient 302 is on treatment table 404. Ultrasound probe 511 may be provided in any suitable manner as by attaching or mounting it to radiation therapy device 400, treatment table 404, gantry 402, or any other available location, provided the position sensing system, or means, 520, can determine the position of ultrasound probe 511 with respect to the radiation therapy device 400. Preferably, position sensing system 520 is a position sensor, such as a 3-D digitizer articulated arm 521. The 3-D digitizer articulated arm 521 is preferably a commercially available, model Microscribe 3DX, 3-D digitizer articulated arm 521 manufactured by Immersion Corporation of San Jose, Calif. Other types of position sensors could be utilized to determine the position of the ultrasound probe 511, or any other type of image generator which is utilized, as will be hereinafter discussed. Examples of such position sensors are: camera systems; retro reflectors; and laser positioning systems, among others.

Articulated arm 321 includes a plurality of sensors (not shown) which track the position and orientation of the first end 522 of arm 521 to which probe 511 is mounted. The output of the sensors in conjunction with computer 490, indicate the position of ultrasound probe 511 with respect to radiation therapy device 400. This position sensing system 520 tracks the position and orientation of the ultrasound probe 511. Position sensing systems other than articulated arm technology, such as 3-D digitizer articulated arm 521, may be used with ultrasound probe 511. Examples of other types of position sensing systems that may be used are those based on: triangulating directional microphones and spark gaps; video camera arrays; and magnetic field orientation.

While the first end 522 of 3-D digitizer articulated arm 521 is connected to ultrasound probe 511, a second end 523 of articulated arm 521 is associated with the base unit 530 which contains some of the circuitry and sensors for articulated arm 521. Base unit 530 also includes a tilt sensor 531 which can indicate if articulated arm is level with respect to gravity, in the event floor 545 is not exactly level, which in turn can also affect the angular disposition of the gantry 402. By use of the tilt sensor 531, the angular disposition of the cart 541, upon which the base unit 530 may be disposed, may be determined; and the angular disposition of the gantry 402 may also be determined, so that the articulated arm 521 may be, aligned, or oriented, to the radiation therapy device, as will be hereinafter described. Disposed between first and second ends 522, 523, is a joint member 524, which assists in articulation of the arm 521. As shown in phantom lines, the first end 522 of articulated arm 521 may be rotated about joint member 524 and the second end 523 of arm 521 can also rotate about base unit 530, as is conventional in the art. Appropriate software associated with 3-D digitizer articulated arm 521, in cooperation with computer 490, permits the operator of the target position verification system 500 to always know the position and orientation of ultrasound probe 511, as will be hereinafter described in greater detail.

Still with reference to FIG. 5, preferably the articulated arm 521 is mounted on a support 540 adjacent treatment table 404. Preferably, support 540 is a moveable support, or cart 541, disposed on a plurality of wheels 542. By mounting articulated arm 521, with its associated ultrasound probe 511 on a moveable support, or cart 541, the target position verification system 500 may be easily placed at its preferred location adjacent treatment table 404. It may also be readily moved away from treatment table 404 at the time the radiation therapy treatment is to begin, and may be conveniently moved and stored out of the way of the radiation therapy device 400. The base unit 530 is preferably firmly attached to the support member 540, or cart 541.

With reference to FIGS. 6–8, the method of the present invention for verifying the position of a target 303 for use in a radiation treatment plan, which includes at least two two-dimensional representations of treatment plan data corresponding to the target 303, will be described. As seen in FIG. 6 the first step 610 is to set up and align, or orient, the 3-D digitizer articulated arm 521 to radiation therapy device 400, in order to align the ultrasound probe 511 to the radiation therapy device 400, coordinate system. By performing this step 610, the geometric orientation, or location, of the ultrasound image generating means 510, or ultrasound probe 511, mounted to articulated arm 521 will be known with respect to the radiation therapy device 400. In turn such geometric orientation will be known for each ultrasound image to be generated. Step 610 can be accomplished by several techniques. Preferably, ultrasound probe 511, mounted upon 3-D digitizer articulated arm 521, may be releasably secured to radiation therapy device 400, as by releasably securing ultrasound probe 511 to gantry 402 or collimator 405 (FIG. 4). A receptacle, or holster, (not shown), may be attached to gantry 402 or collimator 405, and the ultrasound probe 511 may be releasably secured within the receptacle mounted on the gantry 402 or collimator 405. While the ultrasound probe 511, is received within the receptacle, the 3-D digitizer articulated arm 521 operates in a conventional manner, in combination with computer 490 and related software, to indicate where ultrasound probe 511 is geometrically disposed, or located, with respect to radiation therapy device 400. Once ultrasound probe 511 is first oriented with respect to collimator 405, when the gantry 402 is disposed in a known position, the geometric orientation, or location, of ultrasound probe 511 will always be known regardless of where ultrasound probe is located, such as in the location illustrated in FIG. 5 adjacent the patient's body 302. Another technique entails identifying at least three points on gantry 402 by touching 3-D digitizer articulated arm 521 to the points when gantry 402 is at a known position. Yet another technique for aligning 3-D digitizer articulated arm 521 to radiation therapy device 400 includes the step of registering moveable support 540, or cart 541, and the 3-D digitizer articulated arm 521 mounted thereon, to holes 543, or pins 544, on the floor 545 adjacent to treatment table 550, which holes 543 or pins 544 cooperate with the support 540, or with the wheels 542 of cart 541.

The next step 620 involves disposing, or positioning, the patient 560 in a nominal treatment position upon treatment table 404, which preferably approximates the position and orientation the patient 302 had during the imaging process. It should be noted that the set-up step 610 could alternatively follow, rather than precede, the patient positioning step 620.

The next step of the method of the present invention is to generate, or acquire, at least two two-dimensional ultrasound images of the target 303 in the patient's body 302. If only two ultrasound images of the target 303 are taken, they must not be the same image. The two ultrasound images may be any two different ultrasound images of the patient 302 in the room containing the radiation therapy device. Preferably, the at least two ultrasound images are an axial image 700, 800 and a sagittal image 750, 850 (FIGS. 7 and 8) of target 303. These images are generated, or acquired, when ultrasound probe 511 is disposed in the known geometrical orientation, as previously described, through operation of the position sensing system 520, or articulated arm 521. An axial image 700, 800 of target 303 is an image taken in a plane approximately perpendicular to the spinal cord, or longitudinal axis, of the patient 302, as well as perpendicular to the upper surface 438 of treatment table 404, as is known in the art. A sagittal image 750, 850 of target 303 is an image generated in a plane parallel with the longitudinal axis, or spinal cord, of patient 302, as well as being perpendicular and parallel with longitudinal axis of treatment table 404. By rotating ultrasound probe 511 with respect to the second end 522 of articulated arm 521, the desired axial and sagittal images of target 303 may be generated. After ultrasound images 700, 800, 750, 850, of the target 303 are taken by ultrasound probe 501, they may then be frozen and displayed on the screen 1000 of monitor 495, as will hereinafter be described in greater detail.

Instead of utilizing at least two ultrasound images of patient 302, other types of images can be utilized in the method of the present invention. For example, instead of ultrasound images, a gamma camera (not shown) could be used as an image generator and could be used to image radioisotope labeled targets 303 in the patient 302. Alternatively, the images could be plain x-rays or fluoroscopic images displaying patient anatomy with, or without, implanted markers. Any two different images, of many different types, of the patient 302 in the room containing the radiation therapy device could be used. Further, if the radiation treatment plan data is what is known as a center slice two-dimensional radiation treatment plan, and if the center of the target 303, or organ, can be matched with a single two dimensional slice image, the method and apparatus of the present invention as hereinafter described, may be also utilized to verify the position of the target 303.

After at least two images, such as images 700, 750 have been frozen and displayed on screen 1000, the next step 640 of the method of the present invention is to display at least two two-dimensional representations of treatment plan data corresponding to target 303, and then manipulate, or align, the displayed representations of treatment plan data with respect to the displayed ultrasound images, such as images 700, 750, or images 800, 850, as will be hereinafter described in greater detail. The radiation treatment plan can include various types of two-dimensional representations of treatment plan data, in a conventional manner, such as dose distribution contours 710, 740 (FIG. 7), and structure contours 810, 840 (FIG. 8), as is known in the art. The underlying treatment plan data may be a three-dimensional representation of data which is converted into a two-dimensional representation. Additionally, the radiation treatment plan can generate two-dimensional representations of geometric information concerning radiation beam projections and isocenter location (not shown) which may also be displayed on screen 1000 of monitor 495. The two-dimensional representations of treatment plan data can also include actual CT or MR images of the patient 302. In general, the term "treatment plan data" can include any images or data that can be used to generate, evaluate, or create, a radiation treatment plan. As shown on the left side of FIG. 7, an axial ultrasound image 700 of the prostate of patient 302 is displayed and an axial dose distribution contour 710 associated with the patient's prostate in the radiation treatment plan data has been displayed and overlaid, or aligned, with the ultrasound image 700. Similarly, on the right side of FIG. 7 a sagittal ultrasound image 750 of the patient's prostate, or target 303, has been displayed, along with the display of a sagittal dose distribution contour 740. Similarly, in FIG. 8, axial and sagittal ultrasound images 800, 850 are displayed, with axial and sagittal structure contours 810, 840 being also displayed, and aligned with or overlaid upon the ultrasound images 800, 850.

The operator, or user, of the target position verification system 500 may align, or manipulate, the representations of treatment plan data, or dose distribution contours 710, 740, or structure contours 810, 840 with respect to the ultrasound images 700, 750, or images 800, 850, using the arrow keys 1010, if the displayed treatment plan data is not initially displayed in an aligned relationship with the displayed ultrasound images. By manipulating, or aligning, the treatment plan data by use of arrow keys 1010 of computer 490, computer software associated with computer 490 can determine the amount of movement necessary to dispose the target 303, or prostate, of patient 302 with respect to the radiation therapy device 400, to conform the location of target 303 to the desired position of the target 303 in the radiation treatment plan. The computer software determines the necessary amount, type, and direction, of movement of treatment table 404 in order to achieve the desired location of the target 303 in the radiation treatment plan. Alternatively, an amount, type and direction of movement of the radiation therapy device 400 and/or patient 302 can also be determined. The arrow keys 1010 are defined for the couch, or treatment table, 404 motion directions of up, down, in, out, right, and left, and the output of that process is the set of offsets in treatment table position required to realize the desired positioning of the target 303 in the radiation treatment plan. This step allows real-time correlation, display, and alignment of target 303 with patient 302 coordinate system and two-dimensional representations of treatment plan data from the radiation treatment plan.

By utilizing at least two ultrasound images, with at least two of the at least two ultrasound images not being the same image, the computer software can determine the necessary set of offsets in three dimensions as previously described. It should be noted that if only one ultrasound image is utilized, the computer software could determine a set of two dimensional offsets which could be useful in some medical applications, including some radiation treatment plans.

Still with reference to FIG. 6, the next step 650 is to reposition, or move, the treatment table, or couch, 404, the gantry 402, and/or collimator 405, according to the necessary amount, type, and direction, of movement of the treatment table 404, gantry 402, and/or collimator 405, determined by computer 490, in order to conform the desired position of target 303 in the radiation treatment plan. If desired, the patient's body 302 may also be repositioned to achieve proper rotational and/or tilt alignment.

The next step 660 is to verify the alignment, or position, of the target 303, as by repeating steps 630, 640, and step 650 if necessary. Once treatment table 404 has been repositioned, the system 500 is used again in real-time mode to verify proper alignment at the new treatment table 404 position. The operator repeats step 630 to see whether the dose distribution and structure contours, or two-dimensional representations of treatment plan data, align with the ultrasound images. If the images and the contours, or two-dimensional representations of treatment plan data, do not align, the step 640 and 650 may be repeated until the desired position of the target 303 has been obtained.

At that point in time, the next step 670, will be to deliver the desired radiation treatment. The method of the present invention may also include the step of storing the treatment plan data, representations of treatment plan data, and ultrasound images, for use in future procedures, which would include patient set-up, operator verification, physician review, and/or patient records purposes. The method and system 500 of the present invention may also include the utilization and providing of a digital camera (not shown) to take a picture of the patient 302 while on treatment table 404 to record the patient's identity, equipment set-up, and patient orientation, which can be stored in computer 490 for future use.

It is to be understood that the invention is not to be limited to the exact details of construction, operation, exact materials, or embodiments shown and described, as obvious modifications and equivalents will be apparent to one skilled in the art. For example, the method and system of the present invention could be used for patient contour position validation and dosimeter placement for delivery validation using anthropomorphic phantoms. With the ultrasound probe removed from the articulated arm, the arm may be aligned to the gantry coordinate system, and can then be used to provide dose, structure, and contour information from the treatment planning system for the point at the end of the arm. Accordingly, the invention is therefore to be limited only by the scope of the appended claims.

We claim:

1. A method for verifying the position of a target within a body of a patient for use in a radiation treatment plan which includes at least two two-dimensional representations of treatment plan data corresponding to the target, comprising the steps of:

(a) disposing the patient on a treatment table of a radiation therapy device;

(b) providing an ultrasound probe mounted to a 3-D digitizer articulated arm;

(c) generating at least two two-dimensional ultrasound images of the target in the patient's body, with the ultrasound probe being disposed in a known geometric orientation for each ultrasound image generated with the ultrasound probe disposed outside the body of the patient;

(d) displaying the ultrasound images of the target;

(e) displaying the representations of treatment plan data;

(f) aligning the displayed representations of treatment plan data with the displayed ultrasound images; and (g) determining an amount and type of movement of the treatment table and/or radiation therapy device and/or patient required to dispose the target, with respect to the radiation therapy device, to conform to the desired position of the target in the radiation treatment plan.

2. The method of claim 1, wherein the displayed representations of treatment plan data includes at least one dose distribution contour.

3. The method of claim 1, wherein the displayed representations of treatment plan data includes at least one structure contour.

4. The method of claim 1, wherein the displayed representations of treatment plan data is geometric information concerning radiation beam projections and isocenter locations.

5. The method of claim 1, including the step of moving the treatment table with respect to the radiation therapy device to dispose the target to conform to the desired position of the target in the radiation treatment plan.

6. The method of claim 5, fuither including the step of repositioning the patient with respect to the treatment table to achieve rotational or translational alignment of the patient.

7. The method of claim 6, wherein at least one of the ultrasound images is a sagittal image, and the sagittal image is utilized to guide the repositioning of the patient to achieve rotational alignment of the patient.

8. The method of claim 5, including repeating steps (c) through (g).

9. The method of claim 8, including the step of storing the treatment plan data, representations of treatment plan data, and ultrasound images, for use in future procedures, including patient set-up, operator verification, physician review of patient records.

10. The method of claim 1, including the step of disposing the 3-D digitizer articulated arm upon a moveable support.

11. The method of claim 1, including the step of disposing the ultrasound image generating means in the known geometric orientation by aligning the 3-D digitizer articulated arm to the radiation therapy device.

12. The method of claim 11, wherein the radiation therapy device has a collimator, and the 3-D digitizer articulated arm is aligned to the radiation therapy device by releasably securing the 3-D digitizer articulated arm to the collimator.

13. The method of claim 11, wherein the radiation therapy device has a gantry and the 3-D digitizer articulated arm is aligned by identifying at least three points on the gantry by touching the 3-D digitizer articulated arm to the at least three points when the gantry is at a known position.

14. The method of claim 11, including the steps of disposing the 3-D digitizer articulated arm upon a moveable support, providing holes in the floor adjacent the treatment table, and aligning the 3-D digitizer articulated arm by registering the moveable support and the 3-D digitizer articulated arm to the holes.

15. The method of claim 1, wherein the at least two two-dimensional ultrasound images include an axial image and a sagittal image.

16. The method of claim 1, including the step of associating a tilt sensor with a position sensing system associated with the means for generating the ultrasound image.

17. A target position verification system for use by a user with a radiation therapy device for treating a target within a body of a patient and with a radiation treatment plan which includes at least two two-dimensional representations of treatment plan data with the location of the target in the representations of the treatment plan data being known, comprising:

(a) an ultrasound probe for generating at least two two-dimensional ultrasound images of the target;

(b) a position sensing system for indicating the position of the ultrasound probe with respect to the radiation therapy device, the position sensing system including a 3-D digitizer articulated arm having a first and a second end and the ultrasound probe is mounted to the first end of the 3-D digitizer articulated arm, whereby the location of the target with respect to the radiation therapy device is known; and (c) a computer having a monitor associated therewith, adapted to:

(i) display on the monitor the ultrasound images of the target;

(ii) display on the monitor the representations of treatment plan data;

(iii) in response to user input, align the representations of treatment plan data with the ultrasound images; and (iv) in response to the alignment, determine the difference between the location of the target in the ultrasound images and the location of the target in the representations of treatment plan data.

18. The system of claim 17, wherein the second end of the 3-D digitizer arm is associated with a moveable support.

19. The system of claim 17, including a tilt sensor associated with the position sensing system.

20. A method for verifying the position of a target within a body of a patient for use in a radiation treatment plan which includes at least two two-dimensional representations of treatment plan data corresponding to the target, comprising the steps of:

(a) disposing the patient on a treatment table of a radiation therapy device;

(b) providing an ultrasound image generator mounted to a 3-D digitizer articulated arm;

(c) generating at least two two-dimensional ultrasound images of the target in the patient's body, with the ultrasound image generator being disposed in a known geometric orientation for each ultrasound image generated with the ultrasound generator disposed outside the body of the patient;

(d) displaying the ultrasound images of the target;

(e) displaying the representations of treatment plan data;

(f) aligning the displayed representations of treatment plan data with the displayed ultrasound images; and (g) determining an amount and type of movement of the treatment table and/or radiation therapy device and/or patient required to dispose the target, with respect to the radiation therapy device, to conform to the desired position of the target in the radiation treatment plan.

21. The method of claim 20, wherein the displayed representations of treatment plan data includes at least one dose distribution contour.

22. The method of claim 20, wherein the displayed representations of treatment plan data includes at least one structure contour.

23. The method of claim 20, wherein the displayed representations of treatment plan data is geometric information concerning radiation beam projections and isocenter locations.

24. The method of claim 20, including the step of moving the treatment table with respect to the radiation therapy device to dispose the target to conform to the desired position of the target in the radiation treatment plan.

25. The method of claim 24, further including the step of repositioning the patient with respect to the treatment table to achieve rotational or translational alignment of the patient.

26. The method of claim 25, wherein at least one of the ultrasound images is a sagittal image, and the sagittal image is utilized to guide the repositioning of the patient to achieve rotational alignment of the patient.

27. The method of claim 24, including repeating steps (c) through (g).

28. The method of claim 27, including the step of storing the treatment plan data, representations of treatment plan data, and ultrasound images, for use in future procedures, including patient set-up, operator verification, physician review of patient records.

29. The method of claim 20, including the step of utilizing an ultrasound image probe as the ultrasound image generator.

30. The method of claim 29, including the step of disposing the 3-D digitizer articulated arm upon a moveable support.

31. The method of claim 29, including the step of disposing the ultrasound image generator in the known geometric orientation by aligning the 3-D digitizer articulated arm to the radiation therapy device.

32. The method of claim 31, wherein the radiation therapy device has a collimator, and the 3-D digitizer articulated arm is aligned to the radiation therapy device by releasably securing the 3-D digitizer articulated arm to the collimator.

33. The method of claim 31, wherein the radiation therapy device has a gantry and the 3-D digitizer articulated arm is aligned by identifying at least three points on the gantry by touching the 3-D digitizer articulated arm to the at least three points when the gantry is at a known position.

34. The method of claim 31, including the steps of disposing the 3-D digitizer articulated arm upon a moveable support, providing holes in the floor adjacent the treatment table, and aligning the 3-D digitizer articulated arm by registering the moveable support and the 3-D digitizer articulated arm to the holes.

35. The method of claim 20, wherein the at least two two-dimensional ultrasound images include an axial image and a sagittal image.

36. The method of claim 20, including the step of associating a tilt sensor with a position sensing system associated with the ultrasound image generator.

37. A target position verification system for use by a user with a radiation therapy device for treating a target within a body of a patient and with a radiation treatment plan which includes at least one two-dimensional representation of treatment plan data with the location of the target in the at least one representation of the treatment plan data being known, comprising:

(a) an ultrasound probe for generating at least one two-dimensional ultrasound images of the target;

(b) a position sensing system for indicating the position of the ultrasound probe with respect to the radiation therapy device, the position sensing system including a 3-D digitizer articulated arm having a first and a second end and the ultrasound probe is mounted to the first end of the 3-D digitizer articulated arm whereby the location of the target with respect to the radiation therapy device is known; and (c) a computer having a monitor associated therewith, adapted to:
  (i) display on the monitor the at least one ultrasound image of the target;
  (ii) display on the monitor the at least one representation of treatment plan data;
  (iii) in response to user input, align the representation of treatment plan data with the ultrasound image; and
  (iv) in response to the alignment, determine the difference between the location of the target in the ultrasound images and the location of the target in the representations of treatment plan data.

38. The system of claim 37, wherein the second end of the 3-D digitizer arm is associated with a moveable support.

39. The system of claim 37, including a tilt sensor associated with the position sensing system.

* * * * *